April 11, 1972 W. J. WILSON ET AL Plant Pat. 3,110
APPLE TREE
Filed Dec. 11, 1969
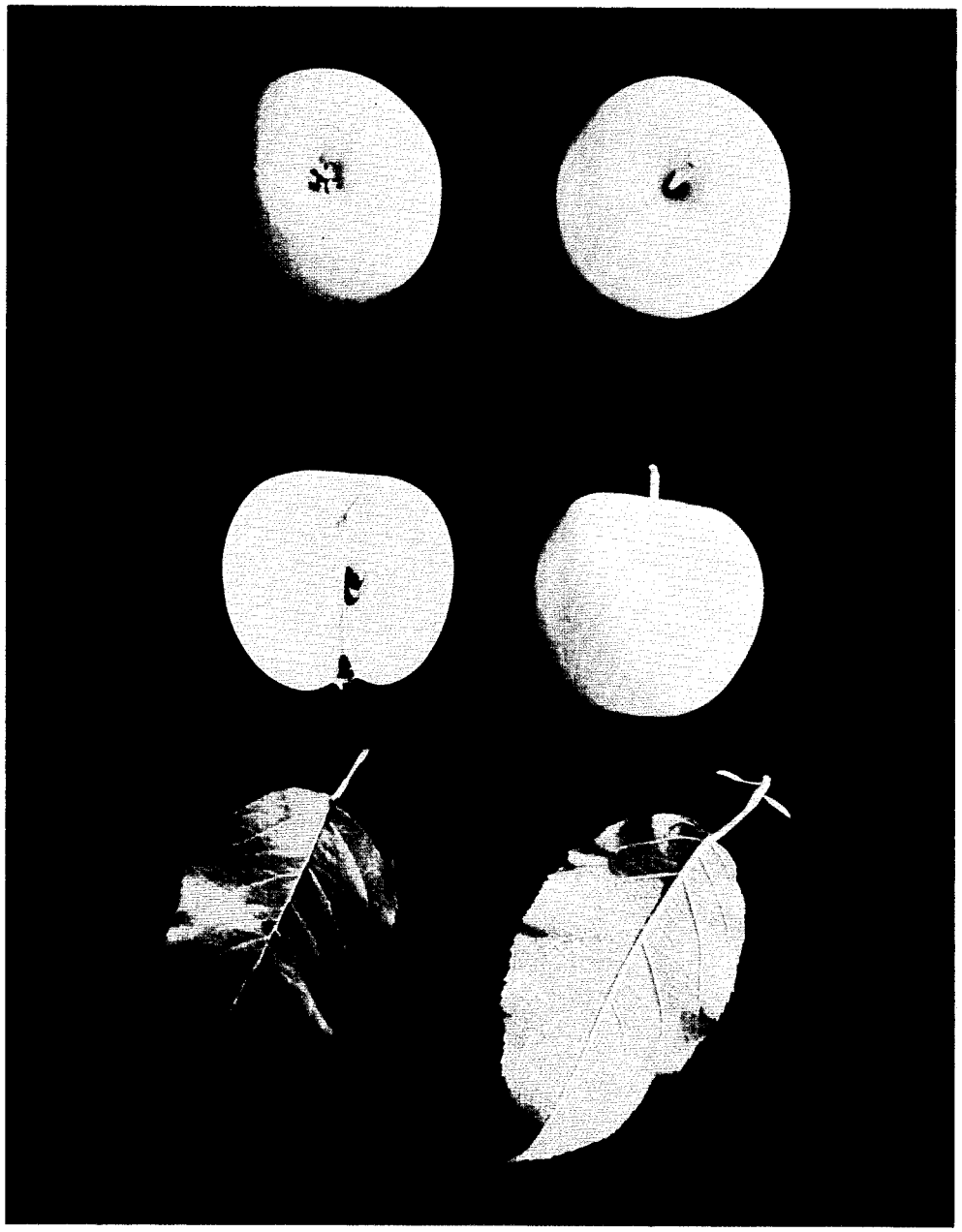
Inventors.
William J. Wilson
Emory Clyde Wilson
By Robert Cobb
Attorneys.

United States Patent Office

Plant Pat. 3,110

Patented Apr. 11, 1972

3,110
APPLE TREE

William J. Wilson and Emory Clyde Wilson, Fort Valley, Ga., assignors to Bountiful Ridge Nurseries, Inc., Princess Anne, Md.

Filed Dec. 11, 1969, Ser. No. 884,389
Int. Cl. A01h 5/03
U.S. Cl. Plt.—34 1 Claim The present invention relates to a new and distinct variety of apple tree which was originated by us as a selected seedling derived from seeds of the apple variety commercially known as "Golden Delicious" (unpatented), which were planted by us on our cultivated fruit farm property located at Fort Valley, Ga.

Previous to this origination, we had been extensively growing trees of the "Golden Delicious" variety, but were progressively losing more and more fruit crops thereof because of excessive russetting of the fruit which made the fruit unsuitable for the commercial market. These losses ran as high as 90% of our "Golden Delicious" crops. We, therefore, began a program of planting seeds of the "Golden Delicious" variety in an effort to produce an improved variety less susceptible to russetting. Our efforts were highly successful, as evidenced by our new seedling which resulted from this program and which was selected by us as being outstanding by reason of the fact that its fruit is almost entirely free of russetting (at least 98% to 99% free) and all fruit thereof is fully marketable. We also found that the new seedling has superior resistance to bitter rot which is a prevalent disease to which other varieties grown under the same conditions are quite susceptible when grown in the same region.

Another unusual and outstanding feature of our new seedling is that when the fruit is very small and at an early stage of growth approximately corresponding to "thumb size," the fruit tends to cluster and become cherry red in color, and later turns yellowish green as the fruit grows to maturity. No other apple variety known to us does this, so it is quite distinctive from a standpoint of identification of our new variety.

Except for the foregoing distinctive features, our new variety is generally similar in most respects to the "Golden Delicious" variety, and asexual propagation of the new variety, as performed by us at Fort Valley, Ga., by both grafting and budding, shows that the characteristics and distinctions are established and come true through succeeding propagations, as observed by us over a prolonged period of years.

The accompanying drawing shows typical specimens of the foliage and fruit of our new variety as depicted in color as nearly true as it is reasonably possible to make the same in a color illustration of this charatcer, said fruit being shown in elevation and also in cross-section, and the foliage specimens depicting both the upper and under surfaces of typical leaves.

The following is a detailed description of the new variety, with color terminology in accordance with Maerz and Paul, Dictionary of Color, except where general color terms of ordinary distionary significance are obvious:

Locality where grown and observed: Fort Valley, Georgia.

Dates of first and last pickings: About August 12 and August 20, respectively.

Tree: Large; vigorous; spreading; tall; open; rapid growing; hardy; very productive; regular bearer.

*Trunk.*—Medium stockiness; medium smooth.

*Branches.*—Medium thickness; smooth; much-branched. Color—Airedale brown, Plate 14–F6. Lenticels—Numerous; medium size.

*Leaves.*—Medium size; long; medium width; ovate; taper-pointed; medium thickness; smooth. Length—About 3⅝ inches. Width—About 2⅛ inches. Color—Near Fir Green, Plate 24–L7. Margin—Coarsely serrate. Petiole—Medium length (about 1 1/16 inches); slender.

Flowers:

*Dates of first and full bloom.*—About April 1 and April 14, respectively; medium early; medium size. Color—White with pale greenish yellow center corresponding to Plate 14–B1.

Fruit:

*Maturity when described.*—Eating hard; about August 12.

*Size.*—Uniform. Axial diameter—About 2¾ inches. Transverse diameter—About 2½ inches.

*Form.*—Uniform; regular; conical.

*Cavity.*—Symmetrical; flaring toward apex. Depth—About ⅜ inch. Breadth—About ⅜ inch. Markings—Light brown coloring.

*Basin.*—Symmetrical; flaring; wide base; even-furrowed.

*Stem.*—Slender. Length—About 1⅛ inches. Bracts—Wanting.

*Calyx.*—Segments persistent; narrowly lanceolate; acuminate; about ⅝ inch long; approximate; erect; connivent.

*Eye.*—Partially closed.

*Skin.*—Thick; smooth; waxy; almost entirely free of russetting. Dots—Obscure; many; even; ruptured. Color—Pale cream, Plate 17–D1 Distribution—About 80% on lower half of each fruit. Ground color—Pale Yellow-Green, Plate 17–L4. Color markings—Blushed. Color—Pale Amber, Plate 12–J3. Bloom—Wanting. General color effect—Light green, with light reddish blush on side exposed to sun.

*Flesh.*—Juicy. Color—Creamy white, Plate 10–E1. Texture—Firm; fine; crisp. Flavor—Sweet; delicate. Aroma—Pronounced. Quality—Good. Core—Median. Bundle area—Small; ovate; symmetrical at base. Halves of core area—Equal. Bundles—Conspicuous. Color—Pale gray-green, Plate 13–K1. Alternate bundle—Approximate to calyx tube. Core lines—Meeting. Cross section—Indistinct; small. Calyx tube—Pubescent; narrowly shouldered; funnel form. Depth of tube to shoulder—About ⅝ inch. Entire depth—about 15/16 inch. Styles—Present; pubescent toward base. Stamens—In one distinct basal whorl. Axillary cavity—Wanting. Seed cells—Axile; closed. Cell walls—Approximate; thick; tough. Length—About ⅝ inch. Breadth—About 3/32 inch. Longitudinal section—Broadly oblong. Surface—Entire. Cross section—Narrow.

Seeds: Usually 10 and all perfect; usually 2 per cell.

*Length.*—About ⅜ inch.

*Breadth.*—About 3/16 inch.

*Form.*—Acuminate.

*Color.*—Bronze, Plate 8–J 12.

Use: Local market; dessert; culinary.

Keeping quality: Good; about 60 days in ordinary storage.

Insect and disease resistance: Good resistance to both insects and diseases as determined by comparison with other apple varieties grown under the same conditions at Fort Valley, Ga.; particularly resistant to bitter rot which is very prevalent in other apple varieties grown in this region.

We claim:

1. A new and distinct variety of apple tree, substantially as herein shown an described, characterized particularly as to novelty by a general resemblance of the tree and fruit in most respects to the apple variety commercially known as "Golden Delicious" (unpatented), but being distinguished therefrom by its more attractive smooth-skinned fruit which is almost entirely free of russeting, superior resistance to bitter rot, and an unusual fruiting habit evidenced by a tendency of the fruit to cluster and acquire a cherry red color when very small, but becoming yellowish green in color as the fruit continues to grow to maturity.

No references cited.

ROBERT B. BAGWILL, Primary Examiner